United States Patent [19]

McKendrick

[11] Patent Number: 4,555,817

[45] Date of Patent: Dec. 3, 1985

[54] PROSTHETIC FOOT AND ANKLE JOINT

[76] Inventor: Roderick W. McKendrick, 336 W. 700 North, Salt Lake City, Utah 84103

[21] Appl. No.: 514,974

[22] Filed: Jul. 18, 1983

[51] Int. Cl.[4] ............................................. A61F 1/04
[52] U.S. Cl. .................................................... 623/40
[58] Field of Search ...................... 3/5, 30, 31, 29, 32, 3/33, 34

[56] References Cited

U.S. PATENT DOCUMENTS

| | | |
|---|---|---|
| 2,643,391 | 6/1953 | McKendrick .............................. 3/2 |
| 3,400,408 | 9/1968 | Garcia ....................................... 3/32 |
| 3,982,280 | 9/1976 | Asbell et al. .............................. 3/32 |
| 4,387,472 | 6/1983 | Wilson ...................................... 3/32 |

OTHER PUBLICATIONS

P. 166A of Catalog of Knit-Rite, Inc., Kansas City, MO.

*Primary Examiner*—Richard J. Apley
*Assistant Examiner*—James Prizant
*Attorney, Agent, or Firm*—Workman, Nydegger & Jensen

[57] ABSTRACT

A foot and ankle joint for a prosthetic appliance has a foot block, an ankle base, and a joint mechanism. The joint includes a resilient block of material such as rubber which is positioned between the foot block and the ankle base. A flexible cable is secured at one end in the ankle base by means of an insert, extends through the rubber block, and is anchored at its other end in the foot block so that the position of the other end is fixed and is not permitted to rotate within the foot block. The components of the foot and ankle block function together to provide the following motions of the foot with respect to the ankle base and connected leg of the user: plantarflexion, dorsalflexion, rotational movement, medial movement, lateral movement and combinations thereof. The foot and ankle joint can be utilized in a conventional or a modular prosthesis.

20 Claims, 2 Drawing Figures

PROSTHETIC FOOT AND ANKLE JOINT

BACKGROUND

1. Field of the Invention

The present invention relates to artificial limbs and, more particularly, to a durable, prosthetic foot and ankle joint which is capable of movement in multiple directions during use, so as to simulate movement of a natural human ankle.

2. The Prior Art

When possible, most foot and leg amputees wear prostheses in order to provide them with greater mobility and to permit them to participate in more activities. In order to perform most effectively and to fulfill its intended purpose, a prosthesis should be comfortable to wear and should simulate the natural movements of the limb and joints it replaces.

A foot prosthesis is generally shaped like a foot so as to fit within ordinary shoes. The prosthesis is generally anchored to the leg of the wearer by a socket member which fits over the stump of the leg. Depending upon the position of the amputation, the prosthesis may include a section which represents a portion of the leg to which the artificial foot is connected.

At the present time, the most common type of foot prosthesis is the SACH (solid ankle, cushioned heel) foot. Because it does not include any movable parts, the SACH foot is the simplest and least expensive prosthesis to build. However, the SACH foot has several drawbacks. For example, inasmuch as the ankle is not jointed, the foot is not capable of any type of rotational or bending movement. Accordingly, a person wearing this type of foot usually walks with a limp.

Additionally, as a person walks and turns during normal use of limbs such as the SACH foot, the socket which secures the prosthesis to the person's leg can rub against the stump. Depending upon the quality of fit between the prosthesis and the stump, this rubbing can cause sores to develop on the stump. These sores can become so severe that a person must remove the prosthesis for extended periods to allow them to heal. Because of the discomfort often experienced with these types of limbs, as well as their inability to provide for rotational or bending movement, many amputees are dissatisfied with the limbs and are seeking something better.

In an effort to eliminate some of the irritation which occurs to the stump of an amputee and to provide greater movement of the foot so that the amputee can participate in a wider range of activities, various attempts have been made to develop movable ankle joints. One such joint provides a single axis of rotation which allows the foot to bend forward and back at the ankle. By providing a single axis of rotation, some of the irritation which occurs during normal walking can be reduced, thereby providing a more natural movement which helps eliminate any limp.

Another modification which has been made to achieve greater flexibility is the inclusion of a device commonly referred to as a rotator. This device is positioned between the foot and the leg of the prosthesis, at the ankle joint. The rotator provides a slight amount of angular rotation about the axis of the ankle so that a person, while having his foot planted, can turn slightly in one direction or another without having to lift or drag the foot. The rotator also facilitates turning while a person is walking.

However, the prior art rotator devices have several drawbacks. First, the inclusion of a rotator in the artificial limb significantly increases the cost of a prosthesis. Second, rotators are relatively heavy, and thus they increase the overall weight of the prosthesis and make it more difficult to walk. Third, rotators, by themselves, only allow rotational movements about the ankle and not other types of desireable movements such as those required for the foot to move forward and back during walking. Hence, still more devices must be included in the prosthesis to allow for such other types of movements.

In light of the foregoing, it is clear that while the inclusion of single axis joints and rotators can increase the flexibility of a foot prosthesis, they still fall far short of adequately simulating the natural movements of an ankle joint.

In an attempt to more closely approximate the features of a normal ankle, an ankle joint was developed which utilized a ball and socket to provide movement of the foot prosthesis in more directions. Such a joint is disclosed in U.S. Pat. No. 2,643,391, issued to Roderick W. McKendrick. This ball and socket joint allows both bending movement as the person walks and also a slight amount of rotational movement. While this joint has solved some of the problems in the prior art, other drawbacks to the use of this joint remain.

For example, the parts of the McKendrick joint have a tendency to wear upon each other as a person uses the joint in walking, thus necessitating frequent repair or replacement of the parts. Additionally, it is common for these joints to develop annoying squeaks as a person walks. It readily becomes clear to a user of this device that, as with the other foot and ankle prostheses presently available, the device often does not provide the full range of desirable capabilities necessary to permit the user to enjoy the desired lifestyle.

Accordingly, what is needed in the art is a foot and ankle joint which is light in weight and which allows movements of the foot in multiple directions, similar to those movements available to a normal foot, while also being sufficiently sturdy to perform under normal use without breakage, excessive wear, or other undesirable side effects such as squeaking. Such a device is disclosed and claimed herein.

BRIEF SUMMARY AND OBJECTS OF THE INVENTION

The present invention is directed to a prosthetic foot and ankle joint which is strong and lightweight and which allows movements similar to those of a normal ankle and foot. In particular, the prosthetic foot and ankle joint is capable of movements such as plantarflexion, dorsalflexion, rotational movement, medial movement, lateral movement and combinations thereof.

A foot block is formed in the general configuration of the human foot with the forward portion being formed from a flexible material so as to provide for bending during use similar to that provided during walking by a normal toe. The foot block is connected to an ankle base by a flexible joint which allows movement of the foot in the direction indicated above. The ankle base is then connected to the shin portion of a prosthesis for attachment to the wearer's leg.

The flexible ankle joint includes a flexible cable which anchors the foot block to the ankle base through a generally cubic block of resilient material (such as rubber) which acts as the resilient means against which the foot block and ankle base operate. The resilient block has one end secured in the foot block and the other end secured in the ankle base. The cable extends through the center of the resilient block and is secured at one end within the foot block and at the other end within the ankle base.

The resilient block allows the foot block and ankle base to move with respect to each other and also supplies the force necessary to return the ankle joint to its normal position once the external forces have been removed. An insert is positioned within the ankle base to secure the cable therein and to provide a means for adjusting the tension on the cable. Thus, the tension on the ankle joint can be adjusted to compensate for the weight of the person and the type of activities in which the user will normally be engaged.

It is, therefore, a primary object of the present invention to provide a foot and ankle joint which is capable of anterior and posterior flexion as well as lateral movements, medial movements and rotation.

It is a further object of the present invention to provide a foot and ankle joint which is strong, and yet is also lightweight in its construction.

Still another object of the present invention is to provide a foot and ankle joint in which the tension can easily be adjusted to require more or less force in causing the joint to move.

Still a further object of the present invention is to provide such a foot and ankle joint which is durable and experiences less wear than other foot and ankle joints, and which thus requires very little maintenance and repair.

It is another object of the present invention to provide a foot and ankle joint having the above-described features which also provides improved comfort to the wearer.

These and other objects and features of the present invention will become more fully apparent from the following description and appended claims taken in conjunction with the accompanying drawings.

DETAILED DESCRIPTION OF THE PREFERRED EMBODIMENT

The present invention is directed to a prosthetic foot and ankle joint which is lightweight, sturdy, and which can bend and turn in directions similar to those of a normal ankle. In order to more fully describe the present invention, reference is next made to the drawings in which like parts are designated with like numerals throughout.

Figure 1:
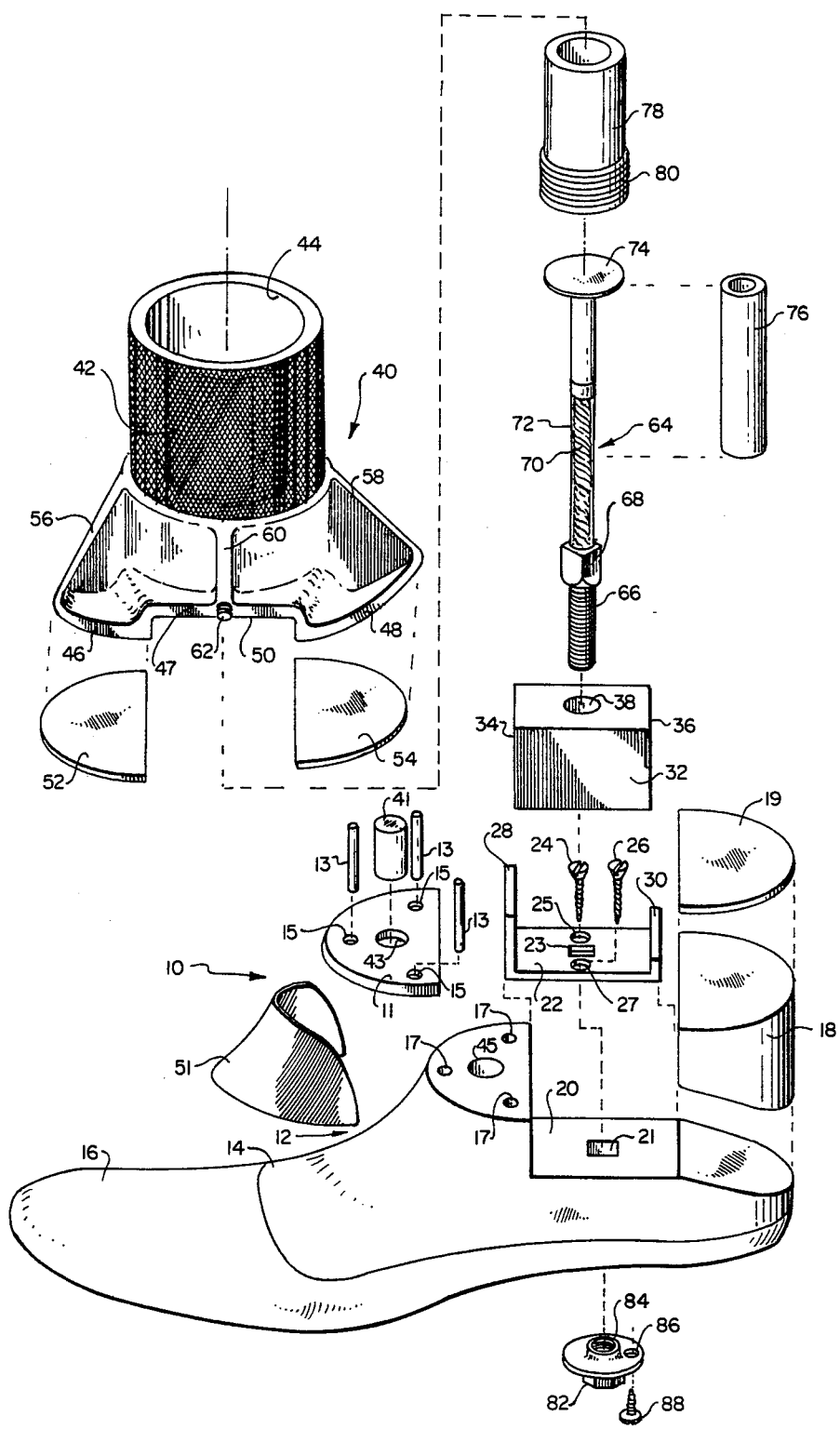
FIG. 1 is an exploded perspective view of a prosthetic foot and ankle joint in accordance with the teachings of the present invention.

Referring first to FIG. 1, a preferred embodiment of the foot and ankle joint of the present invention is generally designated at 10 and is illustrated in an exploded perspective view. Foot and ankle joint 10 has a foot block generally designated at 12 which forms the terminal portion of the foot and ankle joint.

Foot block 12 includes a keel 14 and a sole 16. Keel 14 in the preferred embodiment is formed from a durable wood (such as alderwood), although many other types of materials could also be used with acceptable results. Sole 16 may be formed from oil resistent crape, or from substantially any of the fairly stiff, conventional synthetic rubber products which are commercially available, thereby providing both strength and resiliency in addition to some cushioning to foot and ankle joint 10. The forward end of sole 16 can bend slightly so as to simulate toe motion which occurs while a person is walking.

A keel guard 11 is positioned on top of keel 14 to protect the keel from wear during use. In the preferred embodiment, keel guard 11 is formed from leather and is secured to keel 14 by pegs 13 which pass through holes 15 in guard 11 and through bores 17 in keel 14.

A rubber bumper 41 is positioned in bore 43 which extends through the center of guard 11, and in bore 45 in keel 14. Bumper 41 extends slightly above the upper surface of guard 11 and interacts with the ankle base (discussed more fully hereinafter) to provide controlled toe moment while a person is walking.

A heel 18 is attached to the rear portion of keel 14. Heel 18 is also formed from synthetic rubber and, as more fully discussed hereinafter, allows for natural plantarflexion during walking. A heel guard 19 is positioned on top of heel 18 to protect the heel from wear during use. Heel guard 19 can be formed from leather or any other suitable material which wears well.

Foot block 12 and heel 18 can be formed in any size and are shaped to generally correspond to the contour of a natural foot. Thus, foot and ankle joint 10 can be worn with a common shoe or can be covered with a synthetic skin to resemble a natural foot.

A synthetic skin not only improves the cosmetic appearance of a prosthetic foot but also protects it from dirt and water which can easily damage a foot. Foot block 12 can also be formed in other configurations such that it can be used with other types of shoes. For example, one configuration of a woman's foot can be shaped for flat shoes while another woman's foot can be shaped for use with heels.

A recess 20 is formed in the top of keel 14 forward of heel 18. Recess 20 forms the socket into which is anchored the mechanism of the present invention which provides the ankle motion.

A square bracket shaped housing 22 is positioned in the bottom of recess 20. Housing 22 is anchored in recess 20 by screws 24 and 26 which pass through holes 25 and 27 respectively and are threadably secured within keel 14. Housing 22 has an aperture 23 formed in the center thereof through which passes a cable 64 which holds the ankle joint together. As discussed more fully hereinafter, aperture 23 is square shaped in cross-section in the preferred embodiment to prevent the cable from turning once it is in place.

Extending upwardly so as to comprise the forward end of housing 22 is a flange 28. Flange 28 extends from the bottom of recess 20 to the top of keel 14. Extending upwardly so as to comprise the rear edge of housing 22 is a flange 30. Flanges 28 and 30 prevent the ankle mechanism from turning and also protect keel 14 and heel 18 from undue wear. In a preferred embodiment, housing 22 is formed from aluminum which is strong yet relatively light so as not to add a substantial amount of weight to the prosthesis.

A resilient ankle piece 32 is conformably received and positioned within housing 22. Ankle piece 32 serves as the joint about which the ankle can move and provides the biasing force which restores the prosthesis to its normal position after any external forces are removed. Thus, ankle piece 32 functions in conjunction with other components of foot and ankle joint 10 to provide for movement of the foot in orientations such as plantarflexion, dorsalflexion, rotational movement, medial movement, lateral movement and combinations thereof.

In the preferred embodiment, ankle piece 32 may be formed from one of the many types of high density synthetic rubber which are commercially available, but it could also be formed from natural rubbers or other materials which possess the necessary strength and resiliency. Ankle piece 32 has a generally cubic shape and fits snugly within housing 22. Flanges 28 and 30 of housing 22 prevent the bottom of ankle rubber 32 from turning as the top of ankle piece 32 is twisted during use. A bore 38 is formed through the center of rubber 32 and, when assembled, is in alignment with aperture 23 in housing 22.

Figure 2:
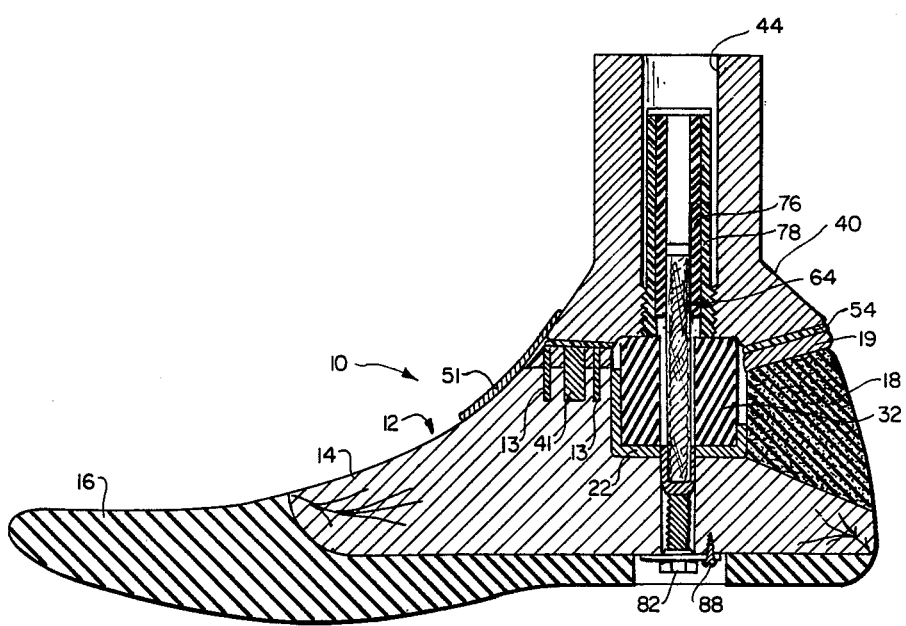
FIG. 2 is a cross-sectional view of the assembled foot and ankle joint of the present invention illustrated in FIG. 1.

An ankle base generally designated at 40 is positioned on top of ankle piece 32 (see FIG. 2). Base 40 includes a generally cylindrical body 42 having a bore 44 extending axially through said base. Ankle base 40 is formed from a strong, lightweight material such as the aluminum alloy sold under the name TENZALOY by AFFCO, located at 6th and Jefferson, Anaconda, Mont. 59711. Base 40 cooperates with ankle piece 32 to allow the various ankle movements. When the foot block 12 is planted on the ground and a force is exerted on ankle base 40, the flexibility of ankle piece 32 allows the ankle base to move in a direction determined by the force, while the foot block remains substantially fixed.

Base 40 also serves to connect foot and ankle joint 10 to the shin of the prosthesis. When used in conjunction with a modular prosthesis, base 40 is connected directly to the shin portion of the prosthesis. When utilized in connection with a conventional prosthesis, base 40 can be covered with suitable blocks and a synthetic skin-like material so as to give the appearance of the lower portion of a shin.

The bottom portion of base 40 extends outwardly to form a front bumper 46 and a rear bumper 48. A protective pad 52 is placed on the bottom of front bumper 46. Pad 52 is formed from TEFLON ® (a registered trademark of DuPont Corporation) in the preferred embodiment and protects bumper 46, keel guard 11, and bumper 41 from wear during use. A similar pad 54 is placed on the bottom of rear bumper 48 to reduce wear between rear bumper 48 and guard 19 on heel 18.

A perpendicular flange 56 is formed above front bumper 46 and is anchored to cylinder 42 to provide added strength to bumper 46. A similar flange 58 is formed above rear bumper 48 and a side flange 60 is formed above the web 45 which connects bumper 46 and 48. A similar side flange is formed on the other side of ankle base 40.

A recess 50 is formed in the bottom of ankle base 40 between bumpers 46 and 48 and is designed to securely fit over the top of ankle piece 32. Thus, when foot and ankle joint 10 is in its assembled configuration, ankle piece 32 is securely held between ankle base 40 and foot block 12. When a synthetic skin is used to cover the assembled foot and ankle joint 10, an ankle base guard 51 is also attached to keel 14 to cover the gap between keel guard 11 and front bumper 46. Ankle base guard 51 functions to prevent the skin from becoming caught and damaged in the joint as the ankle bends.

Ankle base 40 is secured to foot block 12 by a cable generally designated at 64. Cable 64 includes a lower threaded portion 66, an anchoring portion 68, a flexible fiber cable portion 70 which is encased within a plastic covering 72, and a head 74.

Cable 64 is designed to fit through an axial bore 82 in the center of an insert 78 which itself is threadably secured in the base 44 of ankle block 40 by threads 80. The head 74 of cable 64 is sized such that it cannot pass through the bore 82 extending axially through insert 78. A rubber sleeve 76 is placed around the upper portion of cable 64 below head 74 which is positioned within insert 78 after assembly. Sleeve 76 acts as a shock absorber between insert 78 and cable 64.

After passing through insert 78, cable 64 passes through bore 38 in ankle piece 32 and also extends through aperture 23 of plate 22 and bore 21 in keel 14. In the preferred embodiment, anchor 68 of cable 64 is generally square shaped in cross-section as are bore 23 in plate 22 and bore 21 in keel 14. Thus, when anchor 68 is positioned in bores 23 and 21, it cannot rotate but is held securely in position.

Cable 64 is secured in place on the bottom of foot block 12 by a nut 82. Nut 82 includes a radially enlarged portion 84 on the upper section thereof to serve as a washer to prevent nut 82 from screwing into foot block 12. Radially enlarged portion 84 includes an aperture 86 through which a small screw 88 can pass to anchor nut 82 in a fixed position with respect to foot block 12. Thus, once nut 82 has anchored cable 64 in place, neither the lower end of the cable nor the nut can turn or otherwise function to cause the device to come apart. Additionally, inasmuch as cable 64 and nut 82 are independently held in position and prevented from turning, nut 82 can also be used to adjust the tension on cable 64.

Insert 78 is held in position within ankle base 40 by threads 80 formed in the bottom of insert 78. Threads 80 correspond with threads formed in the bottom of axial bore 44 in ankle base 40. Insert 78 can also be used to make major adjustments in the tension of foot and ankle joint 10. By screwing insert 78 higher into base 40, the tension on cable 64 is increased, thus increasing the amount of force necessary to cause movements in the foot and ankle joint. Because insert 78 is removeable from the lower end of the ankle base, the cable may also be removed through that lower end for repair or replacement. Thus, the insert not only functions as an anchor for the upper end of the cable and as a means of adjusting tension in the device, but it also provides a means by which the cable may be removeably accessed easily.

In order to secure insert 78 in its adjusted position, a set screw 62 is positioned in the side of ankle base 40. Set screw 62 extends through one wall of cylindrical body 42 so that the forward end of set screw 62 can abut against insert 78 and secure that insert in place.

Reference is next made in FIG. 2 which illustrates the assembled foot and ankle joint 10 in cross-section. The present invention is a significant improvement over the prior art in that it provides an ankle joint of simple design which is capable of movement in many directions similar to the movements of a normal ankle. As a person walks forward, the forward portion of sole 16 which is made from material such as rubber can bend slightly, thus simulating the normal toe action as a person walks. Additionally, ankle base 40 can pivot forward and backward in plantarflexion and dorsalflexion to simulate the normal bending movement of the ankle.

Ankle piece 32 provides a resilient force against which this bending movement operates and restores ankle base 40 and foot block 12 to their normal, preflexed position once all external forces are released.

The amount of plantarflexion and dorsalflexion which can occur is dependent to a great degree upon the tension which is placed on cable 64. By tightening the tension on cable 64, the amount of plantarflexion and dorsalflexion which can occur is decreased. The tension on cable 64 is adjusted by loosening set screw 62 (see FIG. 1) in ankle base 40 and by screwing insert 78 either upward or downward within bore 44. As insert 78 is screwed upward, it pushes against head 74 of cable 64 thus increasing the tension on cable 64. Additionally, the tension on cable 64 can be increased or decreased by removing screw 88 which secures nut 82 in place and by tightening or loosening nut 82 on the threaded portion 66 of cable 64.

When an amputee has the sole 16 of foot and ankle joint 10 planted firmly on the ground and tries to make a turn, ankle base 40 can rotate in either a clockwise or counterclockwise direction with respect to foot block 12 about the axis defined by cable 64. The flexibility of ankle piece 32 allows ankle base 40 to twist approximately 20 degrees in either a clockwise or counterclockwise direction for a total of 40 degrees, yet provides a biasing means to return the ankle base to its normal position once the force is removed. The average human body is only capable of rotating the foot a total of about 28 degrees, or 14 degrees in each direction. This rotation is produced by action in the hip and knee of the normal body, since the natural human ankle is capable of essentially no independent rotation with respect to the connected foot or lower leg. Additionally, because cable 64 and nut 82 are secured in place against rotation, they cannot become loosened as rotational forces are applied to foot and ankle joint 10.

Ankle base 40 is also free to bend laterally with respect to foot block 12. In the preferred embodiment, ankle base 40 can bend approximately 22 degrees in either direction with respect to foot block 12. Because cable 64 is flexible, ankle base 40 and foot block 12 can bend laterally with respect to each other. However, the tension in cable 40 and resiliency of ankle piece 32 return block 12 and base 42 to their respective positions once the external forces have been removed therefrom.

Because of the strong forces exerted upon it, flexible cable 70 must be both very strong and flexible. The cable in a prosthesis for an average adult male must be capable of withstanding forces corresponding to a weight of about one ton without breaking and yet must be flexible enough to allow the bending movements of foot and ankle joint 10.

As can be seen from the foregoing, the present invention provides a unique foot and ankle joint which is durable and lightweight, yet allows movement in essentially all of the directions that a normal ankle can move. Thus, an amputee utilizing the foot and ankle joint of the present invention enjoys greater mobility and can participate in a wider range of activities without having to be burdened by awkward movements. In addition, the components of the foot and ankle joint function together without significant rubbing or other interplay between their surfaces, thus minimizing wear and overcoming the squeaking problem experienced by some prior art devices.

From the foregoing description it will be appreciated that the novel prosthetic foot and ankle joint disclosed herein clearly overcomes many of the longstanding problems in the art by: (1) providing a means by which the artificial foot may move in many directions with many types of motion including plantarflexion, dorsalflexion, rotational movement, medial movement, lateral movement and combinations thereof; (2) providing a foot and ankle joint which is strong, and yet which is also lightweight in construction; (3) providing a foot and ankle joint which permits easy access to the components thereof for repaid and maintenance purposes, and which also permits easy adjustment of the tension between the components so that the amount of force causing the joint to move can be controlled; (4) providing a foot and ankle joint which is durable and experiences only minimal wear and, thus, which requires very little maintenance and repair; and (5) providing such a foot and ankle joint which gives greater comfort to the user by, among other things, reducing the amount of rubbing on the stump and thus reducing the development of sores on the stump.

While the present invention has been described with reference to the presently preferred embodiment as illustrated in FIGS. 1 and 2, the invention may be embodied in other specific forms without departing from its spirit or essential characteristics. The described embodiment is, therefore, considered to be in all respects only as illustrative and not restrictive. The scope of the invention is, therefore, indicated by the appended claims rather than by the foregoing description. All modifications or changes which come within the meaning and range of equivalency of the claims are to be embraced within their scope.

What is claimed and desired to be secured by United States Letters Patent is:

1. A foot and ankle joint for a prosthetic appliance comprising:
    a foot block which provides support for the prosthetic appliance;
    a flexible ankle means adjacent the foot block;
    an ankle base adjacent the ankle means, said ankle base having a bore extending therein;
    an insert disposed within said bore; and
    a cable having a head on one end wherein the cable passes through the insert and the bore, the head of the cable movably resting on the insert and the end of the cable remote from the head, being secured within said foot block so that the foot block, the ankle means, and the ankle base are secured in proper position.

2. A foot and ankle joint as defined in claim 1 wherein the foot block comprises a flexible sole and a substantially rigid keel.

3. A foot and ankle joint as defined in claim 1 wherein the ankle means comprises a resilient member positioned between the foot block and the ankle base.

4. A foot and ankle joint as defined in claim 1 wherein the insert is threadably secured within the bore so that the insert's longitudinal position may be adjusted within said bore by threadable rotation of the insert.

5. A foot and ankle joint as defined in claim 4 further comprising means connectable to the insert for fixing the position of said insert within the bore.

6. A foot and ankle as defined in claim 1 wherein the cable comprises a flexible fiber cable capable of supporting at least one ton of weight without breaking.

7. A foot and ankle joint as defined in claim 1 further comprising means for preventing the lower end of the cable from rotating relative to the foot block when said lower end of the cable is positioned in the foot block.

8. A foot and ankle joint as defined in claim 7 wherein the means for preventing the lower end of the cable from rotating comprises a plug which is connected to the end of the cable remote from the head, and wherein the plug is generally square shaped in cross-section on one end and is positionable in a square-shaped aperture formed in the foot block.

9. A foot and ankle joint as defined in claim 1 wherein the plug is threaded on the second end thereof and is detachably secured in the foot block by a nut which is positioned adjacent the foot block.

10. A foot and ankle joint as defined in claim 1 further comprising a flexible synthetic skin for covering the foot block, the ankle means, and the ankle base.

11. A flexible foot and ankle joint for a prosthetic appliance comprising:
   a foot block forming a terminal portion of the prosthetic appliance;
   an ankle member adjacent the foot block, said ankle member comprising a generally cubic block of resilient material and a flexible cable extending through said resilient material; and
   an ankle base adjacent the ankle member, said ankle base having an insert positioned within a longitudinal bore formed in the ankle base such that the insert movably anchors a first end of the flexible cable within the ankle base, said cable having a head on one end wherein the head of the cable movably rests on said insert, the cable being positioned with respect to the foot block, ankle member, and ankle base such that the cable bends during use at a point intermediate along the length of the cable.

12. A flexible foot and ankle joint as defined in claim 11 wherein the flexible cable includes an anchor member positioned on a second end of said cable, and wherein the anchor member is positionable in the foot block to prevent the second end of the cable from rotating with respect to the foot block.

13. A flexible foot and ankle joint as defined in claim 12 wherein the anchor member comprises a plug which is generally square shaped in cross-section so as to be positionable within a square shaped bore formed in the foot block.

14. A flexible foot and ankle joint as defined in claim 13 wherein the flexible cable further comprises a flexible fiber capable of supporting a weight of about one ton without breaking, said flexible fiber being extending within the block of resilient material.

15. A flexible foot and ankle joint as defined in claim 11 wherein the flexible cable comprises a threaded portion located on a second end of the cable, said threaded portion being detachably secured within the foot block by a nut which is positioned adjacent the foot block.

16. A flexible foot and ankle joint as defined in claim 11 wherein the insert is threadably adjustable within the bore in said ankle base and wherein the insert is anchored within the ankle base by a set screw extending through the ankle base such that the set screw abuts the insert.

17. A method for forming a flexible ankle joint between a foot block and an ankle base in a prosthetic appliance, said method comprising the steps of:
   positioning a block of resilient material between the foot block and the ankle base;
   anchoring a first end of a flexible cable having a head within an insert in the ankle base such that the head movably rests on said insert;
   extending the flexible cable through the block of the resilient material; and
   securing a second end of the cable in the foot block.

18. A method for forming an ankle joint as defined in claim 17 further comprising the step of fastening the cable within the foot block such that the second end of the cable is held in a fixed position which does not rotate within the foot block after assembly.

19. A foot and ankle joint as defined in claim 1 wherein said ankle means is capable of plantarflexion, dorsalflexion, rotational movement, medial movement, and lateral movement.

20. A foot and ankle joint as defined in claim 1 wherein the cable is positioned with respect to the foot block, ankle means, cable joint, and insert so that it bends at a point intermediate along the length of the cable.

* * * * *

UNITED STATES PATENT AND TRADEMARK OFFICE
CERTIFICATE OF CORRECTION

PATENT NO. : 4,555,817
DATED : December 3, 1985
INVENTOR(S) : Roderick W. McKendrick It is certified that error appears in the above-identified patent and that said Letters Patent is hereby corrected as shown below:

Column 2, line 10, "desireable" should be --desirable--
Column 4, line 3, "oil resistent" should be --oil-resistant--
Column 6, line 44, "removeable" should be --removable--
Column 6, line 50, "removeably" should be --removably--
Column 8, line 53, "keel" should be --heel--
Column 10, line 6, "extending" should be --extended--

Signed and Sealed this

Twenty-fifth Day of February 1986

[SEAL]

Attest:

DONALD J. QUIGG

Attesting Officer

Commissioner of Patents and Trademarks